US006294690B1

(12) United States Patent
Deering et al.

(10) Patent No.: US 6,294,690 B1
(45) Date of Patent: Sep. 25, 2001

(54) PROCESS FOR PREPARING A CYCLIC AMINO ACID ANTICONVULSANT COMPOUND

(75) Inventors: Carl Francis Deering, Fennville; Kenneth Earl Mennen, Holland, both of MI (US); Robert Ramage, Edinburgh (GB)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/647,401

(22) PCT Filed: Sep. 16, 1998

(86) PCT No.: PCT/US98/19359

§ 371 Date: Nov. 14, 2000

§ 102(e) Date: Nov. 14, 2000

(87) PCT Pub. No.: WO99/18063

PCT Pub. Date: Apr. 15, 1999

Related U.S. Application Data

(60) Provisional application No. 60/061,383, filed on Oct. 7, 1997.

(51) Int. Cl.[7] .................................................. C07C 229/00
(52) U.S. Cl. .......................... 562/507; 558/359; 514/529; 514/561
(58) Field of Search ........................... 562/507; 585/277; 564/448, 449

(56) References Cited

U.S. PATENT DOCUMENTS

| | | |
|---|---|---|
| 4,024,175 | 5/1977 | Satzinger et al. . |
| 4,087,544 | 5/1978 | Satzinger et al. . |
| 4,152,326 | 5/1979 | Hartenstein et al. . |
| 4,894,476 | 1/1990 | Butler et al. . |
| 4,956,473 | 9/1990 | Mettler et al. . |
| 4,958,044 | 9/1990 | Mettler et al. . |
| 4,960,931 | 10/1990 | Butler et al. . |
| 5,025,035 | 6/1991 | Wallace . |
| 5,068,413 | 11/1991 | Steiner et al. . |
| 5,084,479 | 1/1992 | Woodruff . |
| 5,091,567 | 2/1992 | Geibel et al. . |
| 5,095,148 | 3/1992 | Mettler et al. . |
| 5,130,455 | 7/1992 | Mettler et al. . |
| 5,132,451 | 7/1992 | Jennings et al. . |
| 5,136,091 | 8/1992 | Mettler et al. . |
| 5,149,870 | 9/1992 | Mettler et al. . |
| 5,319,135 | 6/1994 | Jennings et al. . |
| 5,362,883 | 11/1994 | Jennings et al. . |
| 5,510,381 | 4/1996 | Pande . |
| 5,629,451 | * 5/1997 | Hearn et al. . |
| 5,693,848 | 12/1997 | Esselborn et al. . |
| 5,792,791 | 8/1998 | Kogami et al. . |
| 6,054,482 | 4/2000 | Augart et al. . |

OTHER PUBLICATIONS

Moody et al Tetrahedron Letters, 1986, 27(43) 5253–5254.*
Griffiths et al. "Novel Synetheses of Gabapentin via Addition of Hydrocyanic Acid to Cyclohexylidenemalonate or Cyano(cyclohexylidene)acetate", *Helvetica Chimica ACTA*, vol. 74, No. 1 (1991): pp. 309–314 XP002100736.
Schultz et al. "Birch Reduction and Reductive Alkylation of Benzonitriles and Benzamides"*Journal of Organic Chemistry*, vol. 51, No. 25 (Dec. 12, 1986): pp. 4983–4987 XP002100737.
Grunberger et al. "Evaluation of encephalotropic and psychotropic properties of gabapentin in man by pharmaco–EEG and psychometry", *International Journal of Clinical Pharmacology, Therapy and Toxicology*, vol. 24, No. 7 (1986): pp. 262–373.

* cited by examiner

*Primary Examiner*—Gary Geist
*Assistant Examiner*—Paul A. Zucker
(74) *Attorney, Agent, or Firm*—Merchant & Gould P.C.

(57) ABSTRACT

An improved process for the preparation of a cyclic amino acid by a novel synthesis is described where benzonitrile is treated with an alkali metal and an amine under Birch reduction conditions to generate in situ an anionic intermediate which is alkylated with an α-haloacetic acid moiety which is subsequently converted to the desired product, as well as valuable intermediates used in the process.

49 Claims, No Drawings

PROCESS FOR PREPARING A CYCLIC AMINO ACID ANTICONVULSANT COMPOUND

This application is a § 371 of PCT/US98/19359 of Sep. 16, 1998, which claims the benefit of provisional application Ser. No. 60/061,383 of Oct. 7, 1997.

BACKGROUND OF THE INVENTION

U.S. Pat. Nos. 4,024,175 and 4,087,544, which are herein incorporated by reference, disclose novel cyclic amino acids of Formula A

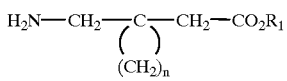

A wherein $R_1$ is a hydrogen atom or a lower alkyl radical, and n is 4, 5, or 6 and the pharmacologically compatible salts thereof:

The compounds disclosed in the above United States patents are useful for the therapy of certain cerebral, diseases, for example, they can be used for the treatment of certain forms of epilepsy, faintness attacks, hypokinesia, and cranial traumas. Additionally, they bring about an improvement of cerebral functions, and thus are useful in treating geriatric patients. Particularly valuable is 1-(aminomethyl) cyclohexaneacetic acid (gabapentin).

Gamma-aminobutyric acid (GABA) is an inhibitory amino acid found in the mammalian central nervous system (CNS). It has been reported that dysfunction with GABA neurotransmission in the CNS may contribute or even cause psychiatric and neurological diseases such as epilepsy, schizophrenia, Parkinson's disease, Huntington's Chorea, and dyskinesia (Saletu B., et al., *International Journal of Clinical Pharmacology, Therapy and Toxicology*, 1986;24:362–373). Gabapentin was designed as a GABA analog that would cross the blood-brain barrier. Gabapentin was found to have anticonvulsant and antispastic activity with extremely low toxicity in man.

U.S. Pat. No 5,084,479 discloses the use of gabapentin in neurodegenerative disorders. U.S. Pat. No. 5,025,035 discloses the use of gabapentin in depression. U.S. Pat. No. 5,510,381 discloses the use of gabapentin in mania and bipolar disorders.

The aforementioned compounds of Formula A including gabapentin have been prepared from a compound of formula

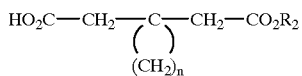

wherein $R_2$ is an alkyl radical containing up to eight carbon atoms, and n is as defined above by well-known standard reactions such as, for example, the Hofmann, Curtius, or Lossen rearrangements into the amino derivatives of Formula A. Although these reactions provide the target compounds, they require a large number of synthetic steps and in some cases involve potentially explosive intermediates.

U.S. Pat. No. 4,152,326 discloses cyclic sulphonyloxy-imides of formula

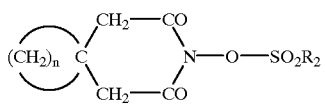

wherein $R_2$ is a saturated, straight-chained, branched or cyclic lower aliphatic radical or an unsubstituted or substituted aryl radical, and n is 4, 5, or 6, which can be converted into a compound of Formula A. Again, similar to the previous processes, this process requires a large number of synthetic steps to obtain a compound of Formula A. Finally, all of the previous processes require as the penultimate step conversion of an intermediate salt of the target compound to an amino acid of Formula A.

U.S. Pat. Nos. 5,132,451, 5,319,135, 5,362,883, 5,091,567, 5,068,413, 4,956,473, 4,958,044, 5,130,455, 5,095,148, 5,136,091, and 5,149,870 disclose additional processes and intermediates for preparing gabapentin. These processes require a number of steps and in some cases utilize large quantities of hazardous materials.

The object of the present invention is an improved process for preparing gabapentin employing a novel synthesis.

Further, we have unexpectedly found that gabapentin can be prepared from novel intermediates in fewer steps and higher yields than the previous methods. Moreover, the present method proceeds from inexpensive starting materials and is amenable to large-scale synthesis.

SUMMARY OF THE INVENTION

Accordingly, a first aspect of the present invention is an improved process for the preparation of the compound of Formula I

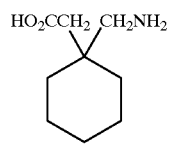

1 which comprises:

Step (a) treating the compound of Formula VII

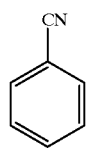

VII with an alkali metal in ammonia or higher order amine in the presence of a solvent to afford in situ the compound of Formula VI

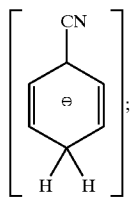

Step (b) treating the compound of Formula VI with a compound of Formula V

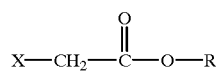

V wherein X is halo or sulfonate and R is hydrogen, an alkali metal, an alkaline earth metal, ammonium, an amine cation, alkyl, or benzyl in the presence of a solvent to afford a compound of Formula IV

IV wherein R is as defined above;
Step (c) treating a compound of Formula IVa

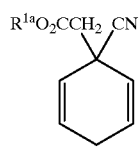

IVa wherein $R^{1a}$ is alkyl with hydrogen in the presence of a catalyst and a solvent to afford a compound of Formula III

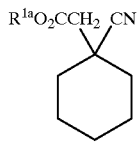

III wherein $R^{1a}$ is as defined above;
Step (d) treating the compound of Formula IIIa

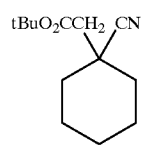

IIIa with an acid in a solvent to afford the compound of Formula II

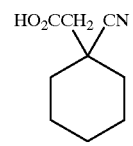

II or treating a compound of Formula IIIb

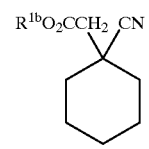

IIIb wherein $R^{1b}$ is alkyl excluding tertiary butyl with an acid or base in a solvent to afford the compound of Formula II or treating the compound of Formula IVb

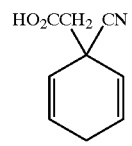

IVb with hydrogen in the presence of a catalyst and a solvent to afford the compound of Formula II or treating the compound of Formula IVc

IVc with hydrogen in the presence of a catalyst and a solvent to afford the compound of Formula II;
Step (e) treating the compound of Formula IVa-1

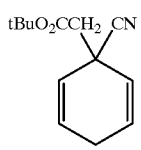

IVa-1 with an acid in a solvent to afford the compound of Formula IVb or treating a compound of Formula IVa-2

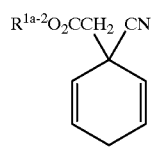

IVa-2 wherein $R^{1a\text{-}2}$ is alkyl excluding tertiary butyl with an acid or base in a solvent to afford the compound of Formula IVb; and Step (f) treating either the compound of Formula IVb or the compound of Formula IVc or the compound of Formula II with hydrogen in the presence of a catalyst and a solvent to afford the compound of Formula I.

A second aspect of the present invention is an improved process for the preparation of a compound of Formula IV

IV wherein R is hydrogen, an alkali metal, an alkaline earth metal, ammonium, an amine cation, alkyl, or benzyl which comprises:

Step (a) treating the compound of Formula VII

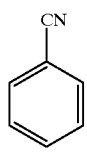

VII with an alkali metal in ammonia or higher order amine in the presence of a solvent to afford in situ the compound of Formula VI

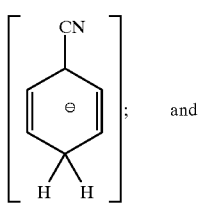

; and

VI

Step (b) treating the compound of Formula VI with a compound of Formula V

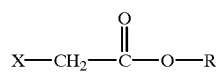

V wherein X is halo or sulfonate and R is hydrogen, an alkali metal, an alkaline earth metal, ammonium, an amine cation, alkyl, or benzyl in the presence of a solvent to afford a compound of Formula IV.

A third aspect of the present invention is an improved process for the preparation of a compound of Formula III

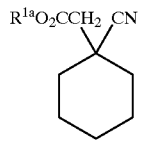

III wherein $R^{1a}$ is alkyl which comprises:

Step (a) treating the compound of Formula VII

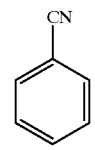

VII with an alkali metal in ammonia or higher order amine in the presence of a solvent to afford in situ the compound of Formula VI

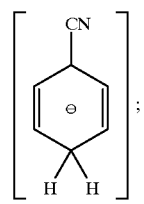

VI

Step (b) treating the compound of Formula VI with a compound of Formula V

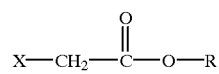

V wherein X is halo or sulfonate and R is hydrogen, an alkali metal, an alkaline earth metal, ammonium, an amine cation, alkyl, or benzyl in the presence of a solvent to afford a compound of Formula IV

IV wherein R is as defined above; and

Step (c) treating a compound of Formula IVa

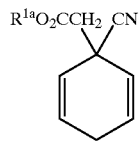

IVa wherein $R^{1a}$ is alkyl with hydrogen in the presence of a catalyst and a solvent to afford a compound of Formula III.

A fourth aspect of the present invention is an improved process for the preparation of the compound of Formula II

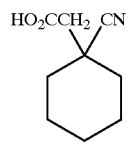

II which comprises:

Step (a) treating the compound of Formula VII

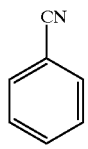

VII with an alkali metal in ammonia or higher order amine in the presence of a solvent to afford in situ the compound of Formula VI

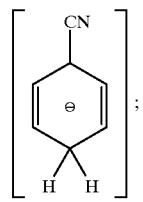

VI

Step (b) treating the compound of Formula VI with a compound of Formula V

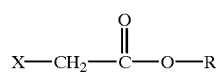

V wherein X is halo or sulfonate and R is hydrogen, an alkali metal, an alkaline earth metal, ammonium, an amine cation, alkyl, or benzyl in the presence of a solvent to afford a compound of Formula IV

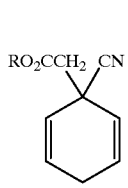

IV wherein R is as defined above;

Step (c) treating a compound of Formula IVa

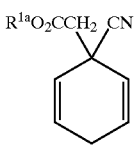

IVa wherein $R^{1a}$ is alkyl with hydrogen in the presence of a catalyst and a solvent to afford a compound of Formula III

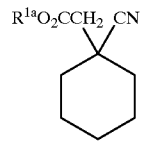

III wherein $R^{1a}$ is as defined above; and

Step (d) treating the compound of Formula IIIa

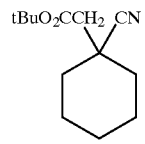

IIIa with an acid in a solvent to afford the compound of Formula II or treating a compound of Formula IIIb

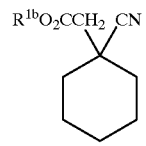

IIIb wherein $R^{1b}$ is alkyl excluding tertiary butyl with an acid or base in a solvent to afford the compound of Formula II or treating the compound of Formula IVb

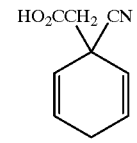

IVb with hydrogen in the presence of a catalyst and a solvent to afford the compound of Formula II or treating the compound of Formula IVc

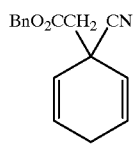

IVc with hydrogen in the presence of a catalyst and a solvent to afford the compound of Formula II.

A fifth aspect of the present invention is an improved process for the preparation of the compound of Formula IVb

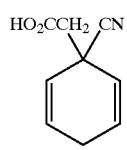

IVb which comprises:

Step (a) treating the compound of Formula VII

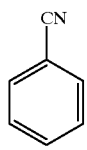

VII with an alkali metal in ammonia or higher order amine in the presence of a solvent to afford in situ the compound of Formula VI

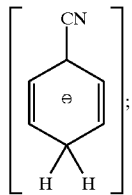

VI

Step (b) treating the compound of Formula VI with a compound of Formula Va

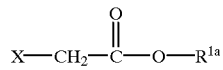

Va wherein X is halo or sulfonate and $R^{1a}$ is alkyl, in the presence of a solvent to afford a compound of Formula IVa

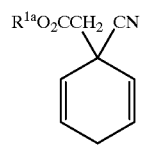

IVa wherein $R^{1a}$ is as defined above; and

Step (c) treating a compound of Formula IVa with an acid or base in a solvent to afford the compound of Formula IVb A sixth aspect of the present invention is an improved process for the preparation of the compound of Formula I

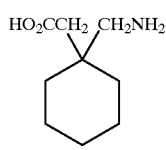

1 which comprises:

Step (a) treating the compound of Formula VII

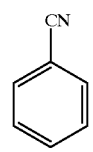

VII with an alkali metal in ammonia or higher order amine in the presence of a solvent to afford in situ the compound of Formula VI

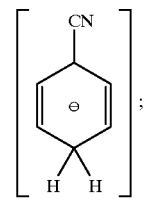

VI

Step (b) treating the compound of Formula VI with a compound of Formula VIII

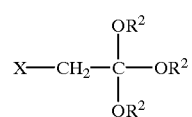

VIII wherein X is halo or sulfonate and $R^2$ is alkyl in the presence of a solvent to afford a compound of Formula IX

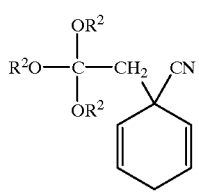

wherein $R^2$ is alkyl;

Step (c) treating a compound of Formula IX with hydrogen in the presence of a catalyst and a solvent to afford a compound of Formula X

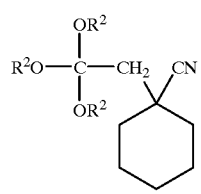

wherein $R^2$ is as defined above;

Step (d) treating a compound of Formula IX with an acid in the presence of a solvent to afford the compound of Formula IVb

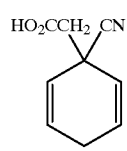

or treating a compound of Formula X with an acid in the presence of a solvent to afford the compound of Formula II

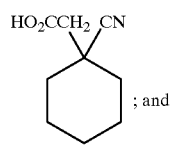

Step (e) treating either the compound of Formula IVb or Formula II with hydrogen in the presence of a catalyst and a solvent to afford the compound of Formula I.

A seventh aspect of the present invention is an improved process for the preparation of a compound of Formula IX

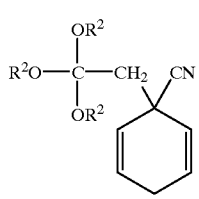

wherein $R^2$ is alkyl which comprises:

Step (a) treating the compound of Formula VII

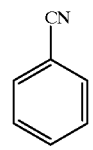

with an alkali metal in ammonia or higher order amine in the presence of a solvent to afford in situ the compound of Formula VI

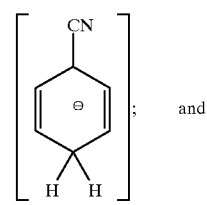

Step (b) treating the compound of Formula VI with a compound of Formula VIII

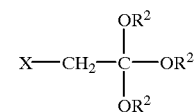

wherein X is halo or sulfonate and $R^2$ is alkyl in the presence of a solvent to afford a compound of Formula IX.

An eight aspect of the present invention is an improved process for the preparation of a compound of Formula X

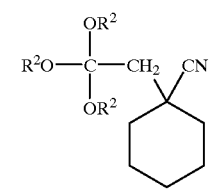

wherein $R^2$ is alkyl which comprises:

Step (a) treating the compound of Formula VII

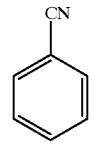

with an alkali metal in ammonia or higher order amine in the presence of a solvent to afford in situ the compound of Formula VI

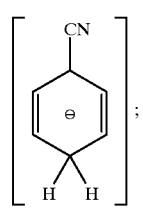

Step (b) treating the compound of Formula VI with a compound of Formula VIII

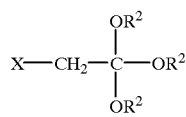

wherein X is halo or sulfonate and $R^2$ is alkyl in the presence of a solvent to afford a compound of Formula IX

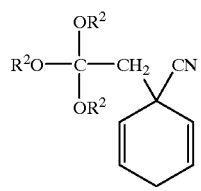

wherein $R^2$ is alkyl; and

Step (c) treating a compound of Formula IX with hydrogen in the presence of a catalyst and a solvent to afford a compound of Formula X.

A ninth aspect of the present invention is an improved process for the preparation of the compound of Formula II

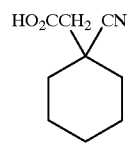

which comprises:

Step (a) treating the compound of Formula VII

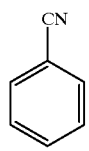

with an alkali metal in ammonia or higher order amine in the presence of a solvent to afford in situ the compound of Formula VI

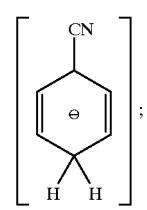

Step (b) treating the compound of Formula VI with a compound of Formula VIII

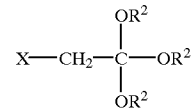

wherein X is halo or sulfonate and $R^2$ is alkyl in the presence of a solvent to afford a compound of Formula IX

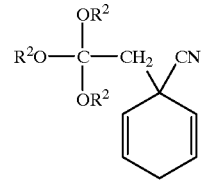

wherein $R^2$ is alkyl;

Step (c) treating a compound of Formula IX with hydrogen in the presence of a catalyst and a solvent to afford a compound of Formula X

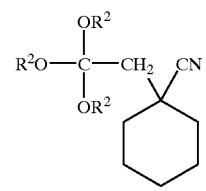

wherein $R^2$ is as defined above; and

Step (d) treating a compound of Formula X with an acid in the presence of a solvent to afford the compound of Formula II.

A tenth aspect of the present invention is an improved process for the preparation of the compound of Formula IVb

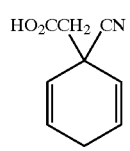

which comprises:

Step (a) treating the compound of Formula VII

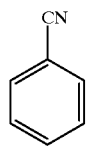                                                VII with an alkali metal in ammonia or higher order amine in the presence of a solvent to afford in situ the compound of Formula VI

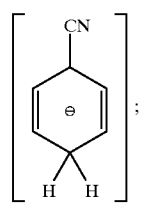                                                VI

Step (b) treating the compound of Formula VI with a compound of Formula VIII

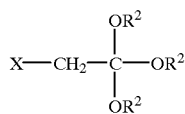                                                VIII wherein X is halo or sulfonate and $R^2$ is alkyl in the presence of a solvent to afford a compound of Formula IX

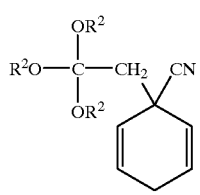                                                IX wherein $R^2$ is alkyl; and Step (c) treating a compound of Formula IX with an acid in the presence of a solvent to afford the compound of Formula IVb An eleventh aspect of the present invention is a novel compound of Formula IV

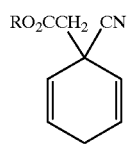                                                IV wherein $R^1$ is hydrogen, an alkali metal, an alkaline earth metal, ammonium, an amine cation, alkyl, or benzyl.

A twelfth aspect of the present invention is a novel compound of Formula IX

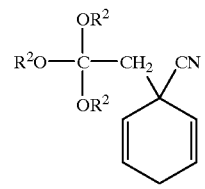                                                IX wherein $R^2$ is alkyl A thirteenth aspect of the present invention is a novel compound of Formula X

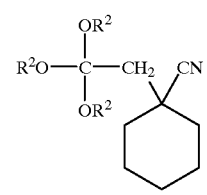                                                X wherein $R^2$ is alkyl.

DETAILED DESCRIPTION OF THE INVENTION

In this invention, the term "alkyl" means a straight or branched hydrocarbon group having from one to twelve carbon atoms and includes, for example, methyl, ethyl, n-propyl, isopropyl, n-butyl, isobutyl, tertiary-butyl, n-pentyl, n-hexyl, n-heptyl, n-octyl, n-nonyl, n-decyl, undecyl, dodecyl, and the like.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, magnesium, and the like.

"Halo" is halogen which is fluorine, chlorine, bromine, or iodine.

"Sulfonate" is tosyl, mesyl, phenylsulfonate, chlorophenylsulfonate, bromophenylsulfonate, methoxyphenylsulfonate, and the like.

"Higher order amine" is methylamine, dimethylamine, methylethylamine, diethylamine, and the like.

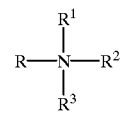

wherein R, $R^1$, $R^2$, $R^3$, are the same or different and each is hydrogen, alkyl of from 1 to 8 carbon atoms, phenyl, tolyl, and the like.

The compounds of Formula I are capable of further forming both pharmaceutically acceptable acid addition and/or base salts. All of thee forms are within the scope of the present invention.

Pharmaceutically acceptable acid addition salts of the compounds of Formula I include salts derived from nontoxic inorganic acids, such as hydrochloric, nitric, phosphoric, sulfuric, hydrobromic, hydriodic, phosphorous, and the like, as well as the salts derived from nontoxic organic acids, such as aliphatic mono and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *Journal of Pharmaceutical Science*, 1977;66:1–19).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free bases for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine (see, for example, Berge S. M., supra.).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acids for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

U.S. Pat. Nos. 4,894,476 and 4,960,931 disclose gabapentin monohydrate and a process for producing the gabapentin monohydrate.

The following table provides a list of abbreviations and definitions thereof used in the present invention:

| DEFINITION | ABBREVIATION |
|---|---|
| Tertiary butyl alcohol | t-BuOH |
| Ammonia | $NH_3$ |
| Trifluoroacetic acid | TFA |
| Tetrahydrofuran | ThF |
| Nitrogen | $N_2$ |
| Ethyl acetate | EtOAc |
| Magnesium sulfate | $MgSO_4$ |
| Dichloromethane | $CH_2Cl_2$ |

-continued

| DEFINITION | ABBREVIATION |
|---|---|
| Proton nuclear magnetic resonance spectroscopy | $^1$H-NMR |
| Deuterated chloroform | $CDCl_3$ |
| Carbon nuclear magnetic resonance spectroscopy | $^{13}$C-NMR |
| Methanol | MeOH |
| Hydrogen | $H_2$ |
| Methyl tertiary butyl ether | MTBE |
| Hydrochloric acid | HCl |
| Palladium on charcoal | Pd/C |
| Ammonium hydroxide | $NH_4OH$ |
| Deuterated methanol | $CD_3OD$ |
| Silicon dioxide (silica) | $SiO_2$ |
| Palladium on barium sulfate | $Pd/BaSO_4$ |
| Vapor phase chromatography | VPC |
| Pounds per square inch | PSI |
| Potassium hydroxide | KOH |
| Sodium hydroxide | NaOH |
| Potassium bromide | KBr |
| Ethanol | EtOH |
| tertiary Butyl | t-Bu |
| Benzyl | Bn |
| Refractive index high performance liquid chromatography | RI HPLC |
| Infrared spectroscopy | IR |
| Deuterium oxide | $D_2O$ |
| Water | $H_2O$ |
| Thin layer chromatography | TLC |

Preferred compounds of Formula IV prepared by the improved process of the first aspect of the present invention are:

(1-Cyanocyclohexa-2,5-dienyl)acetic acid ethyl ester;

(1-Cyanocyclohexa-2,5-dienyl)acetic acid;

(1-Cyanocyclohexa-2,5-dienyl)acetic acid benzyl ester; and (1-Cyanocyclohexa-2,5-dienyl)acetic acid t-butyl ester;

or a pharmaceutically acceptable salt thereof.

Preferred compounds of Formula IX prepared by the improved process of the fifth aspect of the present invention are:

1-(2,2,2-Trimethoxy-ethyl)-cyclohexa-2,5-dienecarbonitrile;

1-(2,2,2-Triethoxy-ethyl)-cyclohexa-2,5-dienecarbonitrile; and 1-(2,2,2-Triisopropoxy-ethyl)-cyclohexa-2,5-dienecarbonitrile.

Preferred compounds of Formula X prepared by the improved process of the fifth aspect of the present invention are:

1-(2,2,2-Trimethoxy-ethyl)-cyclohexanecarbonitrile;

1-(2,2,2-Triethoxy-ethyl)cyclohexanecarbonitrile; and 1-(2,2,2-Triisopropoxy-ethyl)-cyclohexanecarbonitrile.

As previously described, the compound of Formula I is useful for the treatment of certain forms of epilepsy, faintness attacks, hypokinesia, and cranial trauma.

The process of the present invention in its first aspect is a new, improved, economical, and commercially feasible method for preparing the compound of Formula I. Furthermore, the process can be carried out in a two-pot procedure.

The process of the present invention in its first aspect is outlined in Scheme 1.

SCHEME 1

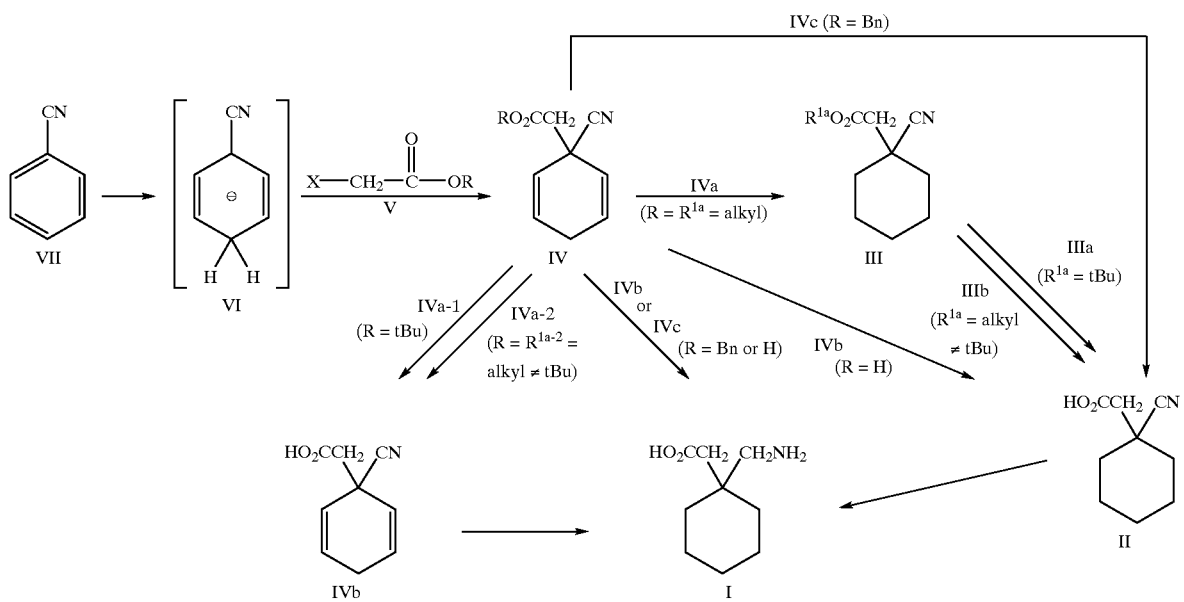

A compound of Formula IV is prepared from benzonitrile (VII) using a Birch reduction, i.e., dissolving metal reduction methodology followed by subsequent alkylation of the anionic intermediate (VI) which is generated in situ.

The alkylation of anions generated in Birch reductions is an established methodology (see "Organic Reactions", ed. Paquette L. A., et al., John Wiley & Sons, New York, N.Y., 1992;42:1–334) in organic synthesis. However, there is only one report of the reductive alkylation of benzonitrile (Schultz A. G. and Macielag M., *Journal of Organic Chemistry*, 1986;51:4983). There is no disclosure of alkylation of these intermediate anions with α-halo acetic acid esters. Though alkylation of nitriles has been disclosed ("Organic Reactions", ed. Dauben W. G., et al., John Wiley & Sons. New York, N.Y., 1984.31:1–364), the alkylation of cyclohexanecarbonitrile and cyclohexanecarbonitrile type compounds with α-halo acetic acid esters has not been reported. We have unexpectedly and surprisingly found that the Birch reduction anionic intermediate (VI) is successfully alkylated with α-haloacetic acid and α-haloacetic acid esters in high yields.

Thus, a solution of benzonitrile in a solvent such as, for example, an alcohol such as tertiary butyl alcohol, ethanol, isopropyl alcohol, tetrahydrofuran, diethyl ether, methyl tertiary butyl ether (MTBE) and the like is treated with an alkali metal such as, for example, lithium, sodium, potassium, and the like an amine such as, for example, ammonia and the like at about −78° C. to about −33° C. for about 0.5 to about 8 hours to generate in situ the anionic intermediate (VI) followed by subsequent treatment with a compound of Formula V wherein X is halo or sulfonate and R is hydrogen, an alkali metal, an alkaline earth metal, ammonium, an amine cation, alkyl, or benzyl to afford a compound of Formula IV wherein R is hydrogen, alkyl, or benzyl. Preferably, the reaction is carried out with lithium in ammonia in tertiary butyl alcohol and tetrahydrofiran.

A compound of Formula IVa wherein R ($R^{1a}$) is alkyl is treated with hydrogen in the presence of a catalyst such as, for example, rhodium on carbon containing palladium, rhodium on carbon containing platinum, rhodium on calcium carbonate containing palladium, rhodium on alumina containing palladium, palladium on carbon, palladium on carbon in the presence of a mineral acid, Raney nickel, and Raney cobalt and the like and a solvent such as, for example, methanol and the like to afford a compound of Formula III wherein $R^{1a}$ is alkyl. Preferably, the reaction is carried out with palladium on charcoal and methanol.

A compound of Formula IIIa ($R^{1a}$ is tertiary butyl [t-Bu]) is treated with an acid such as, for example, hydrochloric acid, hydrobromic acid, trifluoroacetic acid, hydrobromic acid in acetic acid, formic acid, para toluenesulfonic acid, and the like in a solvent such as, for example, dichloromethane, toluene, diethyl ether and the like to afford the compound of Formula II. Preferably, the reaction is carried out with trifluoroacetic acid in dichloromethane.

A compound of Formula IIIb ($R^{1a}$ is alkyl excluding tertiary butyl) is be treated with an acid such as, for example, hydrochloric acid, hydrobromic acid, trifluoroacetic acid, paratoluenesulfonic acid and the like or a base such as, for example, an alkali metal hydroxide such as sodium hydroxide, potassium hydroxide and the like or an alkaline earth metal hydroxide, such as calcium hydroxide and the like in a solvent such as, for example, water and/or an alcohol such as methanol, ethanol and the like to afford the compound of Formula II. Preferably, the reaction is carried out with potassium hydroxide in ethanol.

A compound of Formula IVc (R is benzyl [Bn]) is treated with hydrogen in the presence of a catalyst using the conditions previously described for preparing a compound of Formula III from a compound of Formula IVa to afford the compound of Formula II.

The compound of Formula IVa-1 ($R^1$ is t-Bu) is treated with an acid in the presence of a solvent using the conditions previously described for preparing a compound of Formula II from the compound of Formula IIIa to afford the compound of Formula IVb.

The compound of Formula IVa-2 ($R^1$ is alkyl excluding t-Bu) is treated with an acid or base in the presence of a solvent using the conditions previously described for preparing the compound of Formula II from a compound of Formula IIIb to afford the compound of Formula IVb.

The compound of Formula IVb is treated with hydrogen in the presence of a catalyst using the conditions previously described for preparing a compound of Formula III from a compound of Formula IVa to afford the compound of Formula II.

The compound of Formula IVb, or the compound of Formula IVc, or the compound of Formula II is treated with hydrogen in the presence of a catalyst and a solvent using the conditions previously described for preparing a compound of Formula III from a compound of Formula IVa to afford the compound of Formula I.

The process of the present invention in its fifth aspect is a new, improved, economical, and commercially feasible method for preparing the compound of Formula I. The process of the present invention in its fifth aspect is outlined in Scheme 2.

Compounds of Formula V and Formula VIII are either known or capable of being prepared by methods known in the art.

The following nonlimiting examples illustrate the inventors' preferred method for preparing the compound of the invention.

EXAMPLE 1

1-(Aminomethyl)-cyclohexaneacetic Acid

Method A

Step A: Preparation of (1-Cyanocyclohexa-2,5-dienyl) Acetic Acid Ethyl Ester

Lithium (0.17 g, 24 mmol) was added in portions to a solution of benzonitrile (0.99 mL, 1.0 g, 9.7 mmol) and t-BuOH (0.93 mL, 0.72 g, 9.7 mmol) in $NH_3$ (50 mL) and

SCHEME 2

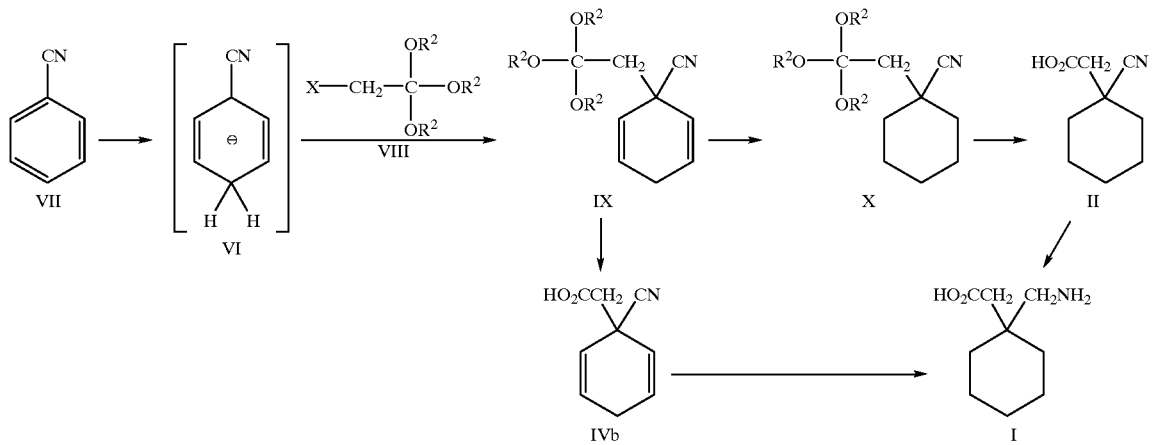

Thus, the anionic intermediate (VI) is generated in situ as described above followed by subsequent treatment with a compound of Formula VIII wherein X is halo or sulfonate and $R^2$ is alkyl using the conditions previously described for preparing a compound of Formula IV from the compound of Formula VI to afford a compound of Formula IX wherein $R^2$ is as defined above.

A compound of Formula IX is treated with hydrogen in the presence of a catalyst and a solvent using the conditions previously described for preparing a compound of Formula III from a compound of Formula IVa to afford a compound of Formula X wherein $R^2$ is as defined above.

A compound of Formula IX is treated with an acid such as, for example, formic acid, acetic acid, hydrochloric acid, hydrobromic acid, trifluoroacetic acid, para toluenesulfonic acid and the like in a solvent such as, for example, dichloromethane, toluene, tetrahydrofuran, diethyl ether and the like to afford the compound of Formula IVb. Preferably, the reaction is carried out with is hydrochloric acid in dichloromethane.

A compound of Formula X is treated with an acid in a solvent using the conditions previously described for preparing the compound of Formula IVb from a compound of Formula IX to afford the compound of Formula II.

The compound of Formula IVb or Formula II is treated with hydrogen in the presence of a catalyst and a solvent using the conditions previously described for preparing a compound of Formula III from a compound of Formula IVa to afford the compound of Formula I.

THF (10 mL) under $N_2$ at −78° C. After 10 minutes, ethyl bromoacetate (2.2 mL, 3.3 g, 20 mmol) was added dropwise. After 1 hour, ammonium chloride (4.0 g, 75 mmol) was added in portions. The reaction mixture was slowly warmed to room temperature while the $NH_3$ was removed with a stream of $N_2$. Water (25 mL) was added, and the mixture extracted with EtOAc (3×25 mL). The combined organic extracts were washed with brine (50 mL), dried ($MgSO_4$), and concentrated under reduced pressure. Flash chromatography ($SiO_2$. $CH_2Cl_2$) afforded 1.12 g (60%) of product as an oil.

$^1$H-NMR ($CDCl_3$): δ 1.28 (t, J=7.1 Hz, 3H), 2.71 (m, 4H), 4.20 (q, J=7.1 Hz, 2H), 5.82 (dt, J=1.9, 10.1 Hz, 2H), 6.01 (dt, J=3.3, 10.1 Hz, 2H); $^{13}$C-NMR ($CDCl_3$): δ 14.2, 25.7, 34.4, 45.1, 61.2, 120.5, 123.6, 128.0, 168.3; IR (neat) 2984, 2231, 1736, 1185 $cm^{-1}$.

Step B: Preparation of (1-Cyanocyclohexyl)acetic Acid Ethyl Ester

Added 1% Pd/C catalyst (1.67 g, 0.157 mmol) to a solution of (1-cyanocyclohexa-2,5-dienyl)acetic acid ethyl ester (3.00 g, 15.7 mmol) in MeOH (75 mL). After shaking the reaction under 20 psi $H_2$ at room temperature for 2 hours, the pressure was slowly released. The reaction was filtered and concentrated under reduced pressure to afford 2.89 g (94%) of product as an oil.

$^1$H-NMR ($CDCl_3$): δ 1.10–1.55 (m, 5H, inc. 1.29, t, J=7.1 Hz), 1.72 (m, 6H), 2.05–2.18 (m, 2H), 2.55 (s, 2H), 4.20 (q, J=7.1 Hz, 2H); $^{13}$C-NMR ($CDCl_3$): δ 14.3, 22.9, 25.2, 35.6, 36.7, 44.5, 61.1, 122.4, 169.1.

Step C: Preparation of (1-Cyanocyclohexyl)acetic Acid (1-Cyanocyclohexyl)acetic acid ethyl ester is reacted with aqueous sodium hydroxide solution using the methodology disclosed at Column 15, Method C, Step B of U.S. Pat. No. 5,132,451 which is herein incorporated by reference to afford the title product.

Step D: Preparation of 1-(Aminomethyl)-cyclohexaneacetic Acid (1-Cyanocyclohexyl)acetic acid is hydrogenated using the methodology disclosed at Columns 14 to 15, Method B, of U.S. Pat. No. 5,132,451 to afford the title compound.

Method B

Step A: Preparation of (1-Cyanocyclohexa-2,5-dienyl)acetic Acid Lithium (0.87 g, 125 mmol) was added in portions to a stirred solution of benzonitrile (5.1 mL, 5.2 g, 50 mmol) and t-BuOH (4.8 mL, 3.7 g, 50 mmol) in THF (5 mL) and $NH_3$ (25 mL). After stirring at −78° C. for 30 minutes, a solution of bromoacetic acid ammonium salt (prepared by mixing bromoacetic acid [13.90 g, 100.0 mmol], THF (15 mL), and $NH_3$ (50 mL) at −78° C. and stirring for 1.5 hours) was added dropwise to the reaction. After stirring at −78° C. for 1 hour, ammonium chloride (20.9 g, 391 mmol) was added in portions. The reaction mixture was slowly warned to room temperature while the $NH_3$ was removed with a stream of $N_2$. Water (75 mL) was added, and the mixture extracted with MTBE (3×50 mL). The stirred aqueous layer was cooled to 0–5° C. acidified to pH=1 with 37% HCl. and extracted with MTBE (3×50 mL). The combined organic extracts of the acidified aqueous layer were dried ($MgSO_4$) and concentrated under reduced pressure to afford 2.49 g (31%) of product as a white solid.

$^1$H-NMR ($CDCl_3$): δ 2.72 (m, 2H), 2.78 (s, 2H), 5.84 (dt, J=1.9, 10.2 Hz, 2H), 6.03 (dt, J=3.3, 10.1 Hz, 2H), 10.41 (broad s, 1H); $^{13}$C-NMR ($CDCl_3$):δ 25.7, 34.2, 44.9, 120.5, 123.4, 128.4, 174.1; IR(KBr) 3051, 2915, 2235, 1719, 1248 $cm^{-1}$.

Step B: Preparation of (1-Cyanocyclohexyl)acetic Acid

Added 5% Pd/C catalyst (0.65 g, 0.31 mmol) to a solution of (1-cyanocyclohexa-2,5-dienyl)acetic acid (0.50 g, 3.1 mmol) and 28% $NH_4OH$ (42.5 μL, 38.3 μg, 0.31 mmol) in MeOH (15 mL). After shaking the reaction mixture under 50 psi $H_2$ at room temperature for 1 hour, the pressure was slowly released. The reaction was filtered and concentrated under reduced pressure to afford 0.48 g (94%) of crude product $^1$H-NMR ($CD_3OD$): δ 1.03–1.59 (m, 7H, theo. 3H), 1.59–1.86 (m, 4H, theo. 5H), 1.96–2.12 (m, 2H), 2.47 (s, 2H), 4.86 (s, 4H, theo. 1H); RI HPLC 63% area.

Step C: Preparation of 1-(Aminomethyl)-cyclohexaneacetic Acid

The title compound is prepared as described in Method A, Step D.

Method C

Step A: Preparation of (1-Cyanocylcohexa-2,5-dienyl)acetic Acid Benzyl Ester

Lithium (0.17 g, 24 mmol) was added in portions to a stirred solution of benzonitrile (0.99 mL, 1.0 g, 9.7 mmol) and t-BuOH (0.93 mL, 0.72 g, 9.7 mmol) in $NH_3$ (50 mL) and THF (10 mL) under $N_2$ at −78° C. After stirring for 15 minutes, benzyl-2-bromoacetate (3.1 mL, 4.5 g, 20 mmol) was added dropwise. After 1 hour, ammonium chloride (4.0 g, 75 mmol) was added in portions. The reaction mixture was slowly warmed to room temperature while the $NH_3$ was removed with a stream of $N_2$. Water (25 mL) was added, and the mixture extracted with EtOAc (3×5 mL). The combined organic extracts were washed with brine (50 mL), dried ($MgSO_4$), and concentrated under reduced pressure. Flash chromatography ($SiO_2$, 1:1–3:1 $CH_2Cl_2$:hexane) afforded 1.79 g (73%) of product as an oil.

$^1$H-NMR ($CDCl_3$): δ 2.60–2.71 (m, 2H), 2.77 (s, 2H), 5.17 (s, 2H), 5.79 (dt, J=1.8, 10.0 Hz, 2H), 5.97 (dt, J=3.3, 9.8 Hz, 2H), 7.37 (m, 5H); $^{13}$C-NMR ($CDCl_3$): δ 25.6, 34.4, 45.0, 67.0, 120.5, 123.4, 128.1, 128.5, 128.6, 128.9, 135.5, 168.1; IR (neat) 3035, 2233, 1738, 1170 $cm^{-1}$.

Step B: Preparation of (1-Cyanocyclohexyl)acetic Acid

Added 5% $Pd/BaSO_4$ catalyst (9.0 mg, 4.2 μmol) to a solution of (1-cyanocyclohexa-2,5-dienyl)acetic acid benzyl ester (1.00 g, 3.95 mmol) in MeOH (20 mL). After stirring the reaction mixture under an atmosphere of $H_2$ at 0° C. for 0.5 hour and room temperature for 1.5 hours, additional 5% $Pd/BaSO_4$ (75.8 mg, 35.6 μmol) was added. After stirring the reaction mixture under an atmosphere of $H_2$ at 0° C. for 1 hour and room temperature for 19.5 hours, the reaction was filtered and concentrated under reduced pressure to afford 0.56 g (87%) of crude oil.

$^1$H-NMR ($CD_3OD$) complex mix showing majority of product; VPC assay 43% area; RI HPLC assay 40% area.

Step C: Preparation of 1-(Aminomethyl)-cyclohexaneacetic Acid (1-Cyanocyclohexyl)acetic acid is hydrogenated according to the procedure of Method A, Step D to afford the title compound.

Method D

Step A: Preparation of (1-Cyanocyclohexa-2,5-dienyl)acetic Acid t-butyl Ester

Lithium (1.73 g, 249 mmol) was added in portions to a stirred solution of benzonitrile (10.2 mL, 10.3 g, 99.9 mmol) and t-BuOH (9.6 mL, 7.4 g, 100 mmol) in $NH_3$ (50 mL) and THF (10 mL) under $N_2$ at −78° C. After stirring for 25 minutes, t-butyl bromoacetate (29.5 mL, 39.0 g, 200 mmol) was added dropwise. After 1 hour, ammonium chloride (41.8 g, 781 mmol) was added in portions. The reaction mixture was slowly warmed to room temperature while the $NH_3$ was removed with a stream of $N_2$. Water (125 mL) was added and the mixture extracted with MTBE (3×50 mL). The combined organic extracts were dried ($MgSO_4$) and concentrated under reduced pressure. Flash chromatography ($SiO_2$, $CH_2Cl_2$-1:14 MTBE:$CH_2Cl_2$) afforded 16.0 g (73%) of product as an oil.

$^1$H-NMR ($CDCl_3$): δ 1.48 (s, 9H), 2.61 (s, 2H), 2.67–2.76 (m, 2H), 5.80 (dt, J=1.9, 10.3 Hz, 2H), 5.99 (dt, J=3.3, 10.2 Hz, 2H); $^{13}$C-NMR ($CDCl_3$): δ 25.6, 28.1, 34.5, 46.3, 82.0, 120.6, 123.8, 127.7, 167.5; IR (neat) 2980, 2232, 1729, 1153 $cm^{-1}$.

Step B: Preparation of(1-Cyanocyclohexyl)acetic Acid t-butyl Ester

Added 5% Pd/C, 50% $H_2O$ catalyst (94.0 mg, 22.1 μmol) to a solution of (1-cyanocyclohexa-2,5-dienyl)acetic acid t-butyl ester (0.50 g, 2.3 mmol) in MeOH (10 mL). After shaking the reaction mixture under 20 psi $H_2$ at room temperature for 18.5 hours, the pressure was slowly released. The reaction was filtered and concentrated under reduced pressure. Flash chromatography ($SiO_2$, 1:3 hexane:$CH_2Cl_2$-100% $CH_2Cl_2$) afforded 0.29 g (56%) of product as an oil.

1H-NMR ($CDCl_3$): δ 1.10–1.45 (m, 4H), 1.49 (s, 9H), 1.60–1.89 (m, 4H), 1.95–2.21 (m, 2H), 2.45 (s, 2H); $^{13}$C-NMR ($CDCl_3$): δ 22.9, 25.2, 28.2, 35.7, 36.8, 45.7, 81.9, 122.6, 168.6; IR (neat) 2935, 2234, 1729, 1368, 1149 $cm^{-1}$.

Step C: Preparation of (1-Cyanocyclohexyl)acetic Acid

To a solution of 2.4 mL (2.4 g, 22 mmol) of anisole in 50 mL of trifluoroacetic acid is added 5.00 g (22.4 mmol) of (1-cyanocyclohexyl)acetic acid, t-butyl ester. The reaction is monitored (TLC) for the loss of starting material and when the reaction is complete it is concentrated under reduced pressure. Water (~10 mL) is added to the residue and the mixture is adjusted to pH=10–12 with base (NaOH). The basic aqueous layer is extracted with a suitable organic solvent (EtOAc) to remove impurities. The aqueous layer is acidified with acid (HCl) to pH=0–4 and extracted with a suitable solvent (EtOAc). The combined organic extracts of the acidified aqueous layer are dried and concentrated under reduced pressure to afford the product.

Step D: Preparation of 1-(Aminomethyl)cyclohexaneacetic Acid (1-Cyanocyclohexyl)acetic acid is hydrogenated according to the procedure of Method A, Step D to afford the title compound.

Method E

Step A: Preparation of (1-Cyanocyclohexa-2,5-dienyl)acetic Acid

Method a:

Added dropwise a solution of KOH (1.73 M, 5.0 mL, 8.7 mmol) in 1:4 $H_2O$:EtOH to a stirred solution of (1-cyanocyclohexa-2,5-dienyl)acetic acid ethyl ester (3.00 g, 15.7 mmol) in EtOH (15 mL) at 0° C. After stirring for 1 hour, a solution of KOH (1.73 M, 5.0 mL, 8.7 mmol) in 1:4 $H_2O$:EtOH was added dropwise. After stirring for 2.5 hours, the reaction was concentrated under reduced pressure. Water (5 mL) was added, and the mixture was extracted with $CH_2Cl_2$ (3×10 mL). The aqueous layer was cooled to 5° C. and acidified to pH=3 with 37% HCl (1.1 mL, 13.4 mmol). The solids were filtered, washed with $H_2O$ (pH=5), and dried under vacuum at room temperature for 16 hours to afford 1.57 g (61%) of the product as a solid.

$^1$H-NMR ($CDCl_3$): δ 2.73 (m, 2H), 2.78 (s, 2H), 5.83 (dt, J=1.9, 10.3 Hz, 2H), 6.03 (dt, J=3.4, 10.4 Hz, 2H), 9.27 (broad s, 1H); $^{13}$C-NMR: δ 25.8, 34.3, 44.8, 120.5, 123.4, 128.4, 173.8.

Method b

To a solution of 2.5 mL (2.5 g, 23 mmol) of anisole in 50 mL of trifluoroacetic acid is added 5.00 g (22.8 mmol) of (1-cyanocyclohexa-2,5-dienyl) acetic acid, t-butyl ester. The reaction is monitored (TLC) for the loss of starting material and when the reaction is complete it is concentrated under reduced pressure. Water (~10 mL) is added to residue and the mixture is adjusted to pH=10–12 base (NaOH). The basic aqueous layer is extracted with a suitable organic solvent (EtOAc) to remove impurities. The aqueous layer is acidified with acid (HCl) to pH=0.4 and extracted with a suitable solvent (EtOAc). The combined organic extracts of the acidified aqueous layer are dried and concentrated under reduced pressure to afford the product.

Step B: Preparation of 1-(Aminomethyl)cyclohexaneacetic Acid

Added 5% Pd/C catalyst (0.33 g, 0.16 mmol) to a solution of (1-cyanocyclohexa-2,5-dienyl)acetic acid (0.25 g, 1.5 mmol) and 28% $NH_4OH$ (70 μL, 63 μg, 0.50 mmol) in MeOH (20 mL). After shaking the reaction mixture under 50 psi $H_2$ at 50° C. for 3.5 hours, the pressure was slowly released, and the reaction was cooled to room temperature. The reaction was filtered and concentrated under reduced pressure to afford 0.27 g (102%) of crude product.

$^1$H-NMR ($D_2O$): δ 1.46 (m, 11H, theo. 10H), 2.43 (s, 2H), 3.00 (s, 2H), 4.78 (s, 4H, theo. 3H); $^{13}$C-NMR ($D_2O$): δ 20.5, 24.8, 33.0, 33.8, 45.4, 47.8, 179.8.

Method F

Preparation of 1-(Aminomethyl)cyclohexaneacetic Acid

Added 5% Pd/C catalyst (0.84 g, 0.40 mmol) to a solution of (1-cyanocyclohexa-2,5-dienyl)acetic acid benzyl ester (1.00 g, 3.95 mmol) and 28% $NH_4OH$ (0.55 mL, 0.50 g, 4.0 mmol) in MeOH (20 mL). After shaking the reaction mixture under 50 psi $H_2$ at 50° C. for 18 hours, the pressure was slowly released, and the reaction was cooled to room temperature. The reaction was filtered and concentrated under reduced pressure to afford 0.63 g (93%) of crude product.

$^1$H-NMR ($CD_3OD$): δ 1.51 (m, 11H, theo. 10H), 2.45 (s, 2H), 2.89 (s, 2H), 4.94 (s, 9H, theo. 3H); RI HPLC 68% area.

Method G

Step A: Preparation of (1-Cyanocyclohexa-2,5-dienyl)acetic acid

The title compound is prepared as described in Method B, Step A.

Step B: Preparation of 1-(Aminomethyl)cyclohexaneacetic acid

The title compound is prepared as described in Method E, Step B.

Method H

Step A: Preparation of (1-Cyanocyclohexa-2,5-dienyl)acetic Acid Ethyl Ester

The title compound is prepared as described in Method A Step A.

Step B: Preparation of (1-Cyanocyclohexa-2,5-dienyl)acetic Acid

The title compound is prepared as described in Method E, Step A.

Step C: Preparation of(1-Cyanocyclohexyl)acetic Acid

The title compound is prepared as described in Method B, Step B.

Step D: Preparation of 1-(Aminomethyl )cyclohexaneacetic Acid

The title compound is prepared as described in Method A, Step D.

What is claimed is:

1. A process for the preparation of the compound of Formula I

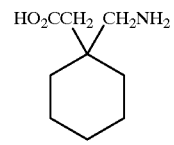

which comprises:

treating either the compound of Formula IVb

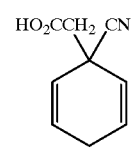

or the compound of Formula IVc

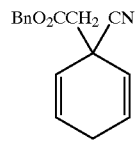

IVc with hydrogen in the presence of a catalyst and a solvent to afford the compound of Formula I.

2. A process for the preparation of the compound of Formula I

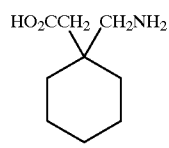

1 which comprises:

Step (a) treating the compound of Formula VII

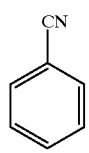

VII with an alkali metal in ammonia or higher order amine in the presence of a solvent to afford in situ the compound of Formula VI

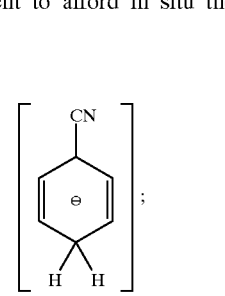

VI

Step (b) treating the compound of Formula VI with a compound of Formula V

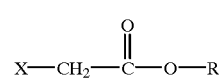

V wherein X is halo or sulfonate and R is hydrogen, an alkali metal, an alkaline earth metal, ammonium, an amine cation, alkyl, or benzyl in the presence of a solvent to afford a compound of Formula IV

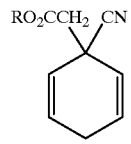

IV wherein R is as defined above;

Step (c) treating a compound of Formula IVa

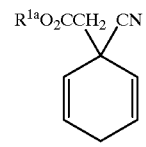

IVa wherein $R^{1a}$ is alkyl with hydrogen in the presence of a catalyst and a solvent to afford a compound of Formula III

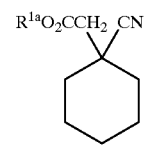

III wherein $R^{1a}$ is as defined above;

Step (d) treating the compound of Formula IIIa

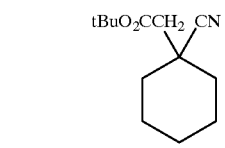

IIIa with an acid in a solvent to afford the compound of Formula II

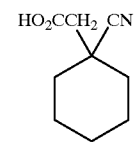

II or treating a compound of Formula IIIb

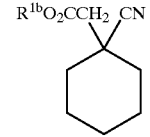

IIIb wherein $R^{1b}$ is alkyl excluding tertiary butyl with an acid or base in a solvent to afford the compound of Formula II or treating the compound of Formula IVb

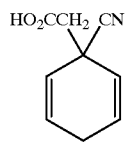

IVb with hydrogen in the presence of a catalyst and a solvent to afford the compound of Formula II or treating the compound of Formula IVc

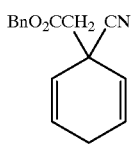

IVc with hydrogen in the presence of a catalyst and a solvent to afford the compound of Formula II;

Step (e) treating the compound of Formula IVa-1

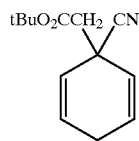

IVa-1 with an acid in a solvent to afford the compound of Formula IVb or treating a compound of Formula IVa-2

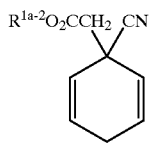

IVa-2 wherein $R^{1a-2}$ is alkyl excluding tertiary butyl with an acid or base in a solvent to afford the compound of Formula IVb; and Step (f) treating either the compound of Formula IVb or the compound of Formula IVc or the compound of Formula II with hydrogen in the presence of a catalyst and a solvent to afford the compound of Formula I.

3. A process according to claim 2 wherein the alkali metal in Step (a) is selected from the group consisting of: lithium, sodium, and potassium.

4. A process according to claim 3 wherein the alkali metal is lithium.

5. A process according to claim 2 wherein the solvent in Step (a) is selected from the group consisting of: ethanol, isopropyl alcohol, tertiary butyl alcohol, tetrahydrofuran, diethyl ether, and methyl tertiary butyl ether.

6. A process according to claim 5 wherein the solvent is a mixture of tertiary butyl alcohol and tetrahydrofuran.

7. A process according to claim 2 wherein the higher order amine in Step (a) is selected from the group consisting of: methylamine, dimethylamine, methylethylamine, and diethylamine.

8. A process according to claim 2 wherein the compound of Formula V in Step (b) is selected from the group consisting of: ethyl bromoacetate, ethyl chloroacetate, bromoacetic acid, chloroacetic acid, bromoacetic acid ammonium salt, chloroacetic acid ammonium salt, benzyl-2-bromoacetate, benzyl 2-chloroacetate, t-butyl bromoacetate, and t-butyl chloroacetate.

9. A process according to claim 2 wherein the solvent in Step (b) is a mixture of tertiary butyl alcohol and tetrahydrofiran.

10. A process according to claim 2 wherein the catalyst in Step (c) is selected from the group consisting of: rhodium on carbon containing palladium, rhodium on carbon containing platinum, rhodium on calcium carbonate containing palladium, rhodium on alumina containing palladium, palladium on carbon, palladium on carbon in the presence of a mineral acid, Raney nickel, and Raney cobalt.

11. A process according to claim 10 wherein the catalyst is palladium on carbon.

12. A process according to claim 2 wherein the solvent in Step (c) is methanol.

13. A process according to claim 2 wherein the acid in Step (d) is selected from the group consisting of: hydrochloric acid, hydrobromic acid, trifluoroacetic acid, hydrobromic acid in acetic acid, formic acid, and para toluenesulfonic acid.

14. A process according to claim 13 wherein the acid is trifluoroacetic acid.

15. A process according to claim 2 wherein the solvent in Step (d) is selected from the group consisting of: dichloromethane, toluene, and diethyl ether.

16. A process according to claim 15 wherein the solvent is dichloromethane.

17. A process according to claim 2 wherein the base in Step (d) is selected from the group consisting of: an alkali metal hydroxide and an alkaline earth metal hydroxide.

18. A process according to claim 17 wherein the base is an alkali metal hydroxide.

19. A process according to claim 18 wherein the base is potassium hydroxide.

20. A process according to claim 2 wherein the acid in Step (e) is selected from the group consisting of: hydrochloric acid, hydrobromic acid, trifluoroacetic acid, hydrobromic acid in acetic acid, and para toluenesulfonic acid.

21. A process according to claim 20 wherein the acid is trifluoroacetic acid.

22. A process according to claim 2 wherein the solvent in Step (e) is selected from the group consisting of: dichloromethane, toluene, and diethyl ether.

23. A process according to claim 22 wherein the solvent is dichloromethane.

24. A process according to claim 2 wherein the base in Step (e) is selected from the group consisting of: an alkali metal hydroxide and an alkaline earth metal hydroxide.

25. A process according to claim 24 wherein the base is an alkali metal hydroxide.

26. A process according to claim 2 wherein the catalyst in Step (f) is selected from the group consisting of: rhodium on carbon containing palladium, rhodium on carbon containing platinum, rhodium on calcium carbonate containing palladium, rhodium on alumina containing palladium, palladium on carbon, palladium on carbon in the presence of a mineral acid, Raney nickel, and Raney cobalt.

27. A process according to claim 26 wherein the catalyst is palladium on carbon.

28. A process according to claim 2 wherein the solvent in Step (f) is methanol.

29. A process for the preparation of a compound of Formula III

III

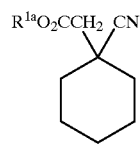

wherein R¹ᵃ is alkyl which comprises:

Step (a) treating the compound of Formula VII

VII

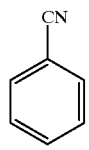

with an alkali metal in ammonia or higher order amine in the presence of a solvent to afford in situ the compound of Formula VI

VI

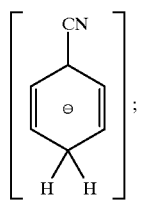

Step (b) treating the compound of Formula VI with a compound of Formula V

V

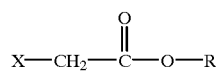

wherein X is halo or sulfonate and R is hydrogen, an alkali metal, an alkaline earth metal, ammonium, an amine cation, alkyl, or benzyl in the presence of a solvent to afford a compound of Formula IV

IV

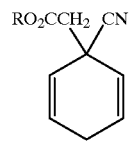

wherein R is as defined above; and

Step (c) treating a compound of Formula IVa

IVa

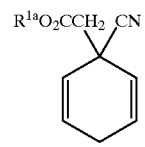

wherein R¹ᵃ is alkyl with hydrogen in the presence of a catalyst and a solvent to afford a compound of Formula III.

30. A process for the preparation of the compound of Formula II

II

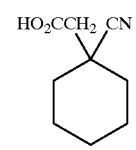

which comprises:

Step (a) treating the compound of Formula VII

VII

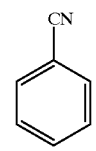

with an alkali metal in ammonia or higher order amine in the presence of a solvent to afford in situ the compound of Formula VI

VI

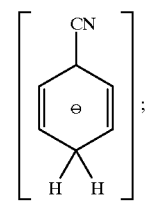

Step (b) treating the compound of Formula VI with a compound of Formula V

V

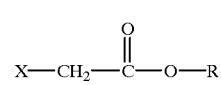

wherein X is halo or sulfonate and R is hydrogen, an alkali metal, an alkaline earth metal, ammonium, an amine cation, alkyl, or benzyl in the presence of a solvent to afford a compound of Formula IV

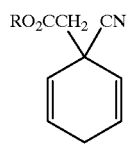
IV wherein R is as defined above;
Step (c) treating a compound of Formula IVa

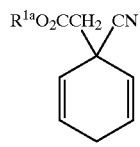
IVa wherein $R^{1a}$ is alkyl with hydrogen in the presence of a catalyst and a solvent to afford a compound of Formula III

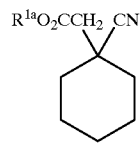
III wherein $R^{1a}$ is as defined above; and
Step (d) treating the compound of Formula IIIa

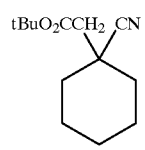
IIIa with an acid in a solvent to afford the compound of Formula II or treating a compound of Formula IIIb

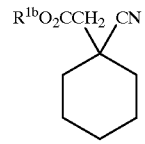
IIIb wherein $R^{1b}$ is alkyl excluding tertiary butyl with an acid or base in a solvent to afford the compound of Formula II or treating the compound of Formula IVb

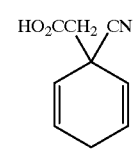
IVb with hydrogen in the presence of a catalyst and a solvent to afford the compound of Formula II or treating the compound of Formula IVc

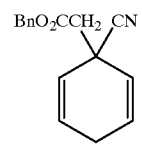
IVc with hydrogen in the presence of a catalyst and a solvent to afford the compound of Formula II.

31. A process for the preparation of the compound of Formula I

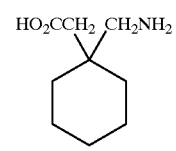
1 which comprises:

Step (a) treating the compound of Formula VII

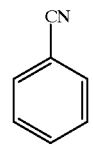
VII with an alkali metal in ammonia or higher order amine in the presence of a solvent to afford in situ the compound of Formula VI

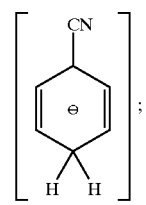
VI

Step (b) treating the compound of Formula VI with a compound of Formula VIII

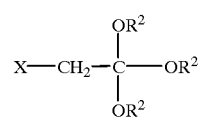
VIII wherein X is halo or sulfonate and $R^2$ is alkyl in the presence of a solvent to afford a compound of Formula IX

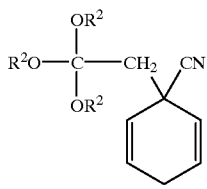

wherein R² is alkyl;

Step (c) treating a compound of Formula IX with hydrogen in the presence of a catalyst and a solvent to afford a compound of Formula X

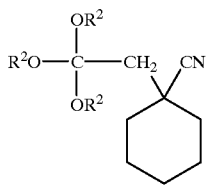

wherein R² is as defined above;

Step (d) treating a compound of Formula IX with an acid in the presence of a solvent to afford the compound of Formula IVb

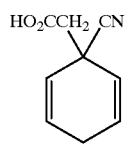

or treating a compound of Formula X with an acid in the presence of a solvent to afford the compound of Formula II

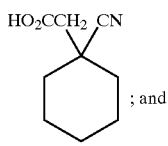
; and

Step (e) treating either the compound of Formula IVb or Formula II with hydrogen in the presence of a catalyst and a solvent to afford the compound of Formula I.

32. A process according to claim 31 wherein the alkali metal in Step (a) is selected from the group consisting of: lithium, sodium, and potassium.

33. A process according to claim 32 wherein the alkali metal is lithium.

34. A process according to claim 31 wherein the solvent in Step (a) is selected from the group consisting of: ethanol, isopropyl alcohol, tertiary butyl alcohol, tetrahydrofuran, diethyl ether, and methyl tertiary butyl ether.

35. A process according to claim 34 wherein the solvent is a mixture of tertiary butyl alcohol and tetrahydrofuran.

36. A process according to claim 31 wherein the solvent in Step (a) is a mixture of tertiary butyl alcohol and tetrahydrofuran.

37. A process according to claim 31 wherein the compound of Formula VIII in Step (b) is selected from the group consisting of: 2-chloro-1,1,1-trimethoxyethane, 2-bromo-1,1,1-trimethoxyethane, 2-chloro-1,1,1-triethoxyethane, 2-bromo-1,1,1-triethoxyethane, 2-chloro-1,1,1-triisopropylethane, and 2-bromo-1,1,1-triisopropylethane.

38. A process according to claim 31 wherein the solvent in Step (b) is a mixture of tertiary butyl alcohol and tetrahydrofuran.

39. A process according to claim 31 wherein the catalyst in Step (c) is selected from the group consisting of: rhodium on carbon containing palladium, rhodium on carbon containing platinum, rhodium on calcium carbonate containing palladium, rhodium on alumina containing palladium, palladium on carbon, palladium on carbon in the presence of a mineral acid, Raney nickel, and Raney cobalt.

40. A process according to claim 39 wherein the catalyst is palladium on carbon.

41. A process according to claim 31 wherein the solvent in Step (c) is methanol.

42. A process according to claim 31 wherein the acid in Step (d) is selected from the group consisting of: formic acid, acetic acid, hydrochloric acid, hydrobromic acid, trifluoroacetic acid, and para toluenesulfonic acid.

43. A process according to claim 41 wherein the acid is hydrochloric acid.

44. A process according to claim 41 wherein the solvent in Step (d) is selected from the group consisting of dichloromethane, toluene, tetrahydrofuran, and diethyl ether.

45. A process according to claim 44 wherein the solvent is dichloromethane.

46. A process according to claim 41 wherein the catalyst in Step (e) is selected from the group consisting of: rhodium on carbon containing palladium, rhodium on carbon containing platinum, rhodium on calcium carbonate containing palladium, rhodium on alumina containing palladium, palladium on carbon, palladium on carbon in the presence of a mineral acid, Raney nickel, and Raney cobalt.

47. A process according to claim 46 wherein the catalyst is palladium on carbon.

48. A process according to claim 41 wherein the solvent in Step (e) is methanol.

49. A process for the preparation of the compound of Formula II

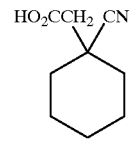

which comprises:

Step (a) treating the compound of Formula VII

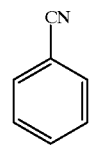

with an alkali metal in ammonia or higher order amine in the presence of a solvent to afford in situ the compound of Formula VI

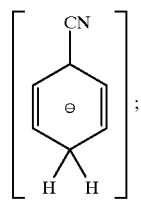

Step (b) treating the compound of Formula VI with a compound of Formula VIII

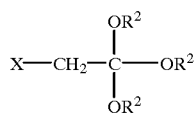

wherein X is halo or sulfonate and $R^2$ is alkyl in the presence of a solvent to afford a compound of Formula IX

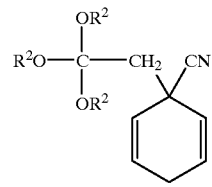

wherein $R^2$ is alkyl;

Step (c) treating a compound of Formula IX with hydrogen in the presence of a catalyst and a solvent to afford a compound of Formula X

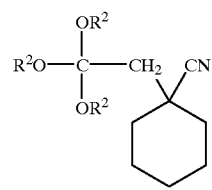

wherein $R^2$ is as defined above; and

Step (d) treating a compound of Formula X with an acid in the presence of a solvent to afford the compound of Formula II.

* * * * *

UNITED STATES PATENT AND TRADEMARK OFFICE
CERTIFICATE OF CORRECTION

PATENT NO. : 6,294,690 B1
DATED : September 25, 2001
INVENTOR(S) : Deering et al.

Page 1 of 1

It is certified that error appears in the above-identified patent and that said Letters Patent is hereby corrected as shown below:

Column 16,
Line 50, before the amine drawing, please insert -- Amine cation is --

Column 20,
Line 33, "is be treated" should read -- is treated --

Column 21,
Line 57, "with is hydrochloric" should read -- with hydrochloric --

Column 23,
Line 14, insert a new paragraph starting with "Lithium"
Line 23, "warned" should read -- warmed --

Column 24,
Line 23, insert a new paragraph starting with "(1-Cyanocyclohexyl)"

Signed and Sealed this

Twenty-first Day of May, 2002

Attest:

Attesting Officer

JAMES E. ROGAN
*Director of the United States Patent and Trademark Office*